US012766160B2

(12) United States Patent
Kim et al.

(10) Patent No.: US 12,766,160 B2
(45) Date of Patent: Oct. 20, 2026

(54) COMPOSITION COMPRISING POLYGALATENOSIDE AS ACTIVE INGREDIENT FOR PREVENTION OR TREATMENT OF CANCER

(71) Applicant: HOSEO UNIVERSITY ACADEMIC COOPERATION FOUNDATION, Asan-si (KR)

(72) Inventors: Sung-Jo Kim, Anyang-si (KR); Hyungkuen Kim, Anyang-si (KR)

(73) Assignee: HOSEO UNIVERSITY ACADEMIC COOPERATION FOUNDATION, Asan-si (KR)

( * ) Notice: Subject to any disclaimer, the term of this patent is extended or adjusted under 35 U.S.C. 154(b) by 376 days.

(21) Appl. No.: 18/697,200

(22) PCT Filed: Nov. 10, 2022

(86) PCT No.: PCT/KR2022/017635
§ 371 (c)(1),
(2) Date: Mar. 29, 2024

(87) PCT Pub. No.: WO2023/128255
PCT Pub. Date: Jul. 6, 2023

(65) Prior Publication Data

US 2024/0408125 A1 Dec. 12, 2024

(30) Foreign Application Priority Data

Dec. 27, 2021 (KR) ........................ 10-2021-0188789

(51) Int. Cl.

| | |
|---|---|
| ***A61K 31/7048*** | (2006.01) |
| ***A61K 8/60*** | (2006.01) |
| ***A61K 9/00*** | (2006.01) |
| ***A61P 35/00*** | (2006.01) |
| ***A61Q 19/08*** | (2006.01) |

(52) U.S. Cl.
CPC .......... *A61K 31/7048* (2013.01); *A61K 8/602* (2013.01); *A61K 9/0053* (2013.01); *A61P 35/00* (2018.01); *A61Q 19/08* (2013.01)

(58) Field of Classification Search
USPC ........................................................... 514/27
See application file for complete search history.

(56) References Cited

U.S. PATENT DOCUMENTS

2008/0076724 A1 3/2008 Cheng et al.

FOREIGN PATENT DOCUMENTS

JP 09-249688 A 9/1997
JP 2006-022081 A 1/2006

OTHER PUBLICATIONS

Bian, Y. et al. "A pectin-like polysaccharide from Polygala tenuifolia inhibits pancreatic cancer cell growth in vitro and in vivo by inducing apoptosis and suppressing autophagy", International journal of biological macromolecules. vol. 162, 2020, pp. 107-115.
Kim, H. et al., "Novel potential NOX2 inhibitors, Dudleya brittonii water extract and polygalatenoside A inhibit intracellular ROS generation and growth of melanoma", Biomedicine & pharmacotherapy. [published online] Apr. 14, 2022, vol. 150, article No. 112967, pp. 1-12.
International Search Report for PCT/KR2022/017635 dated Mar. 6, 2023 (PCT/ISA/210).

*Primary Examiner* — Traviss C McIntosh, III
(74) *Attorney, Agent, or Firm* — Sughrue Mion, PLLC

(57) ABSTRACT

The present invention relates to a composition exhibiting an excellent prophylactic or therapeutic effect on cancer, the composition comprising polygalatenoside, an optical isomer thereof, or a pharmaceutically acceptable salt thereof as an active ingredient. Having the effects of suppressing reactive oxygen, inhibiting NOX2 protein activity, killing cancer cells, and repressing cancer cell growth, the polygalatenoside of the present invention exhibits a prophylactic, alleviative, or therapeutic effect on cancer and thus can be used as a pharmaceutical composition or a food composition for improvement. In addition, the present invention can be used as a food composition or cosmetic composition for improvement exhibiting anti-aging or antioxidant effects due to the suppressive effect on reactive oxygen.

10 Claims, 2 Drawing Sheets

<FIG. 1>
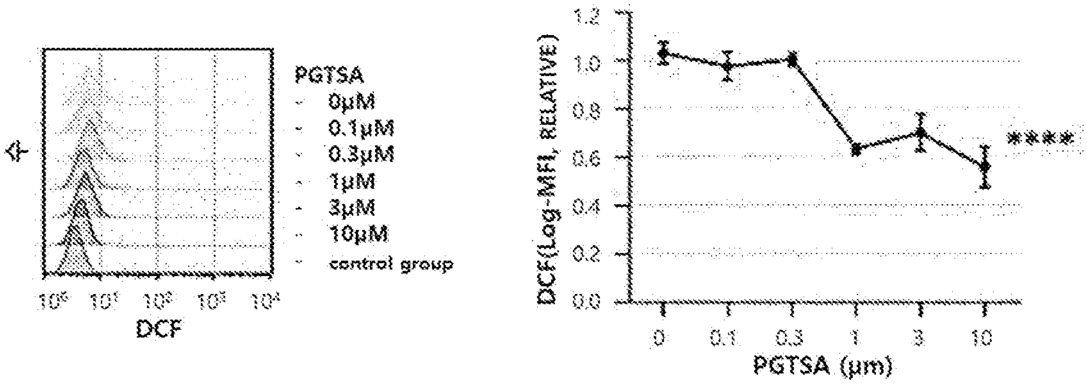
<FIG. 2>
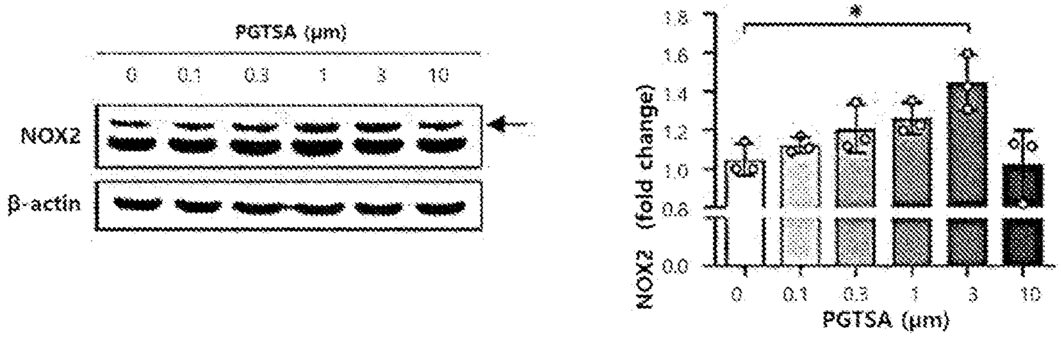

<FIG. 3>
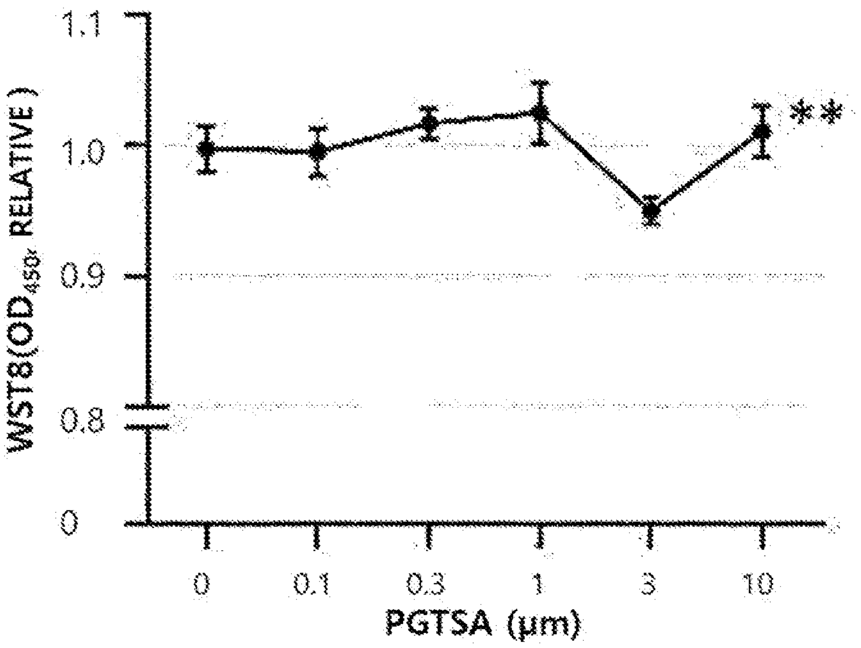
<FIG. 4>
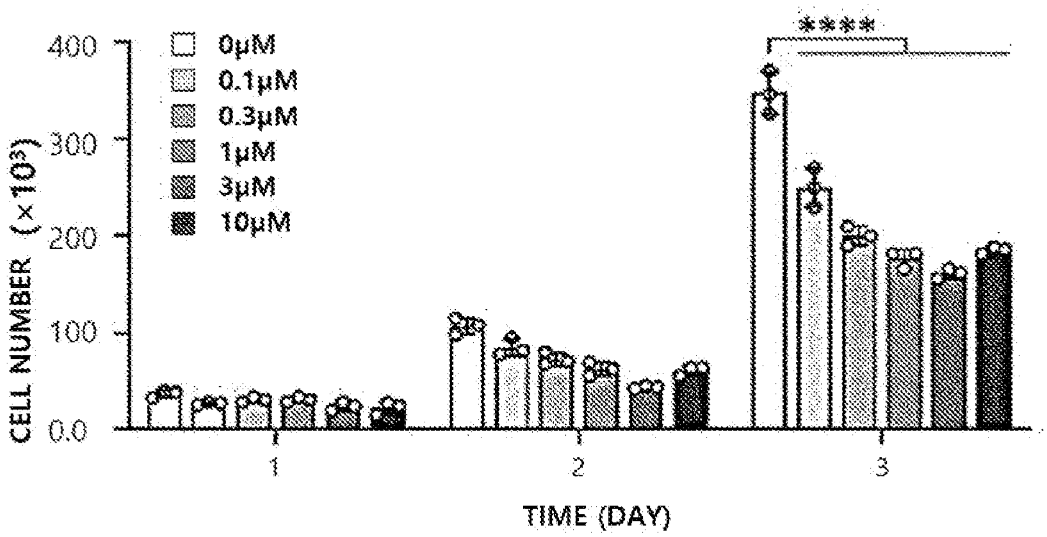

COMPOSITION COMPRISING POLYGALATENOSIDE AS ACTIVE INGREDIENT FOR PREVENTION OR TREATMENT OF CANCER

CROSS REFERENCE TO RELATED APPLICATIONS

This application is a National Stage of International Application No. PCT/KR2022/017635 filed Nov. 10, 2022, claiming priority based on Korean Patent Application No. 10-2021-0188789 filed Dec. 27, 2021, the entire disclosures of which are incorporated herein by reference.

TECHNICAL FIELD

The present invention relates to a composition comprising polygalatenoside as an active ingredient for prevention or treatment of cancer.

BACKGROUND ART

According to "World Population Aging 2017" published by the United Nations (UN), the global elderly population aged 60 or older is 962 million (2017), doubling only in about 37 years compared to 1980. In 2050, about 33 years later, the elderly population will reach approximately 2.1 billion, double the current level, and the increase rate of the elderly population is expected to accelerate. It is expected that even by 2030, about 9 years later from now (in 2021), the elderly population will outnumber children under the age of 10 worldwide. In addition, as the number of patients with geriatric diseases and the burden of medical costs are increasing due to aging, the importance of aging prevention is increasing.

Oxidative stress is known as a main cause of aging, and the oxidative stress contributes to the development of aging-related diseases such as cancer, dementia, neurodegenerative diseases, cardiovascular diseases, and arthritis (Ilaria Liguori et al., Oxidative stress, aging, and diseases, Clinical interventions in aging, 2018; 13: 757-772). NADPH oxidase (NOX) is a membrane-bound enzyme and a major cause of oxidative stress that uses oxygen as a catalyst to generate reactive oxygen and is associated with various diseases. The activity of NOX increases with aging and causes serious oxidative stress in the cardiovascular system. The NOX may regulate the growth and death of cancer cells, such as prostate cancer, pancreatic cancer, melanoma, glioma, breast cancer, bladder cancer, colon cancer, and ovarian cancer. Therefore, NOX inhibition is used as an important strategy for antioxidation, aging prevention, and aging-related disease treatment.

In addition, aging is the most important risk factor for the development of cancer. According to the "National Cancer Institute" in USA, over the past five years (2013-2017), the cancer incidence per 100,000 people has rapidly increased to 25 persons under 20 years old, 350 persons aged 45 to 49, and 1,000 persons aged 60 or older. As cancer treatment technology has advanced, the over 10-year survival rate for some cancers has reached 99%, but there are still cancers, such as pancreatic cancer, with a 10-year survival rate of less than 1%. In addition, compared to cancer treatment technology, the development of technology of preventing cancer is relatively insufficient, and most currently used anticancer drugs have strong side effects.

Conventional anticancer drugs kill cells by directly applying the stress to the cells, resulting in the generation of reactive oxygen, as the cause of oxidative stress. As a result, anticancer drugs may cause various side effects, such as hair loss, vomiting, chills, and decreased immunity, so that the demand for technology of suppressing the generation of reactive oxygen has increased. Most cancer cells increase the level of reactive oxygen, which act as signal transmitters that induce cell growth.

Meanwhile, polygalatenoside was first isolated from *Polygala tenuifolia*, a medicinal plant used as an antipsychotic in China, and therapeutic effects on depression and neurological diseases were reported. The present invention confirmed a prophylactic or therapeutic effect of polygalatenoside on cancer, and thus can be used as a pharmaceutical composition or health functional food composition. In addition, the present invention can be used as a health functional food composition or cosmetic composition that exhibits an anti-aging or antioxidant effect due to the suppressive effect on reactive oxygen.

DISCLOSURE

Technical Problem

An object of the present invention is to provide a pharmaceutical composition comprising polygalatenoside as an active ingredient for prevention or treatment of cancer.

Another object of the present invention is to provide a food composition comprising polygalatenoside as an active ingredient for prevention or alleviation of cancer.

Yet another object of the present invention is to provide a food composition for improvement comprising polygalatenoside as an active ingredient for exhibiting an anti-aging or antioxidant effect.

Yet another object of the present invention is to provide a cosmetic composition for improvement comprising polygalatenoside as an active ingredient for exhibiting an anti-aging or antioxidant effect.

Finally, yet another object of the present invention is to provide a method for treating cancer comprising administering the pharmaceutical composition to a subject.

Technical Solution

The present invention provides a pharmaceutical composition for prevention or treatment of cancer comprising a compound represented by Formula 1 below or a pharmaceutically acceptable salt thereof as an active ingredient.

[Formula 1]

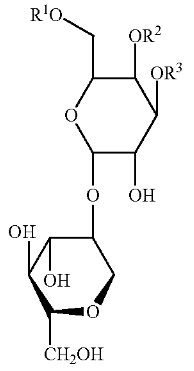

(In Formula 1, $R^1$, $R^2$ and $R^3$ are independently hydrogen atoms or $R^{Bz}$, and at least one of $R^1$, $R^2$ and $R^3$ is $R^{Bz}$, and the $R^{Bz}$ is Formula 2 below.)

[Formula 2]

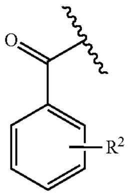

(In Formula 2, $R^2$ is hydrogen atom, halogen, a cyano group, a nitro group, an azide group, a phenyl group, a 5-6 membered heterocyclic group containing one or more heteroatoms selected from the group consisting of N, O and S, a $C_{1-6}$ alkyl group, a $C_{1-6}$ alkoxy group, a $C_{1-6}$ alkylthio group, a $C_{2-6}$ alkenyl group, a $C_{2-6}$ alkynyl group, or a pharmaceutically acceptable salt.)

In an embodiment of the present invention, the compound may be a compound represented by Formula 3 below but is not limited thereto.

[Formula 3]

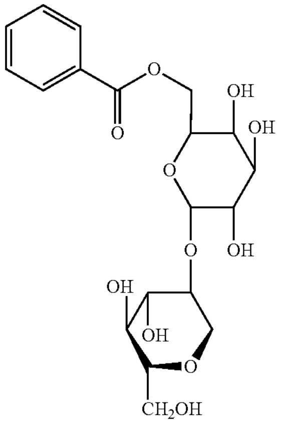

In an embodiment of the present invention, the compound may be a compound represented by Formula 4 below but is not limited thereto.

[Formula 4]

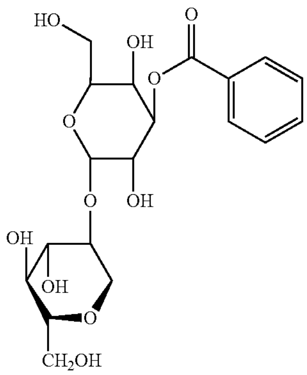

In an embodiment of the present invention, the compound may be a compound represented by Formula 5 below but is not limited thereto.

[Formula 5]

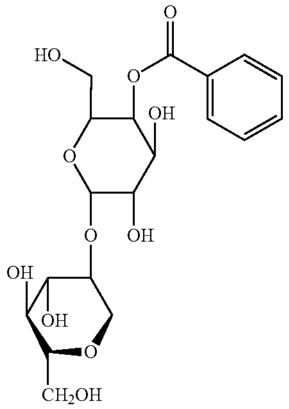

In an embodiment of the present invention, the compound may have an antioxidant effect, but is not limited thereto.

In an embodiment of the present invention, the compound may have an effect of inhibiting NOX2 protein activity but is not limited thereto.

In an embodiment of the present invention, the cancer may be at least one selected from the group consisting of prostate cancer, pancreatic cancer, melanoma, glioma, breast cancer, bladder cancer, colon cancer, and ovarian cancer, but is limited thereto.

The present invention provides a food composition for prevention or palliation of cancer including a compound represented by Formula 1 below, an optical isomer thereof, or a pharmaceutically acceptable salt thereof as an active ingredient.

[Formula 1]

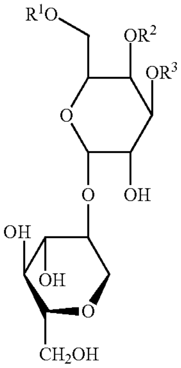

(In Formula 1, $R^1$, $R^2$ and $R^3$ are independently hydrogen atoms or $R^{Bz}$, and at least one of $R^1$, $R^2$ and $R^3$ is $R^{Bz}$, and the $R^{Bz}$ is Formula 2 below.)

[Formula 2]

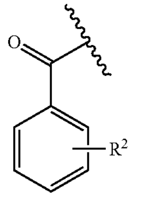

(In Formula 2, $R^2$ is hydrogen atom, halogen, a cyano group, a nitro group, an azide group, a phenyl group, a 5-6 membered heterocyclic group containing one or more heteroatoms selected from the group consisting of N, O and S, a $C_{1-6}$ alkyl group, a $C_{1-6}$ alkoxy group, a $C_{1-6}$ alkylthio group, a $C_{2-6}$ alkenyl group, a $C_{2-6}$ alkynyl group, or a pharmaceutically acceptable salt.)

The present invention provides a food composition for improvement exhibiting an anti-aging or antioxidant effect including a compound represented by Formula 1 below, an optical isomer thereof, or a pharmaceutically acceptable salt thereof as an active ingredient.

[Formula 1]

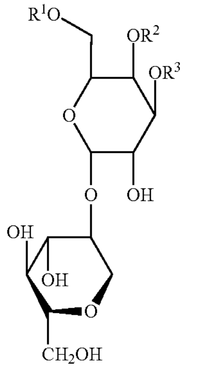

(In Formula 1, $R^1$, $R^2$ and $R^3$ are independently hydrogen atoms or $R^{Bz}$, and at least one of $R^1$, $R^2$ and $R^3$ is $R^{Bz}$, and the $R^{Bz}$ is Formula 2 below.)

[Formula 2]

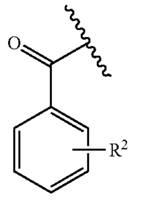

(In Formula 2, $R^2$ is hydrogen atom, halogen, a cyano group, a nitro group, an azide group, a phenyl group, a 5-6 membered heterocyclic group containing one or more heteroatoms selected from the group consisting of N, O and S, a $C_{1-6}$ alkyl group, a $C_{1-6}$ alkoxy group, a $C_{1-6}$ alkylthio group, a $C_{2-6}$ alkenyl group, a $C_{2-6}$ alkynyl group, or a pharmaceutically acceptable salt.)

The present invention provides a cosmetic composition for improvement exhibiting an anti-aging or antioxidant effect including a compound represented by Formula 1 below, an optical isomer thereof, or a pharmaceutically acceptable salt thereof as an active ingredient.

Finally, the present invention provides a method for preventing or treating cancer including administering the pharmaceutical composition to a subject.

[Formula 1]

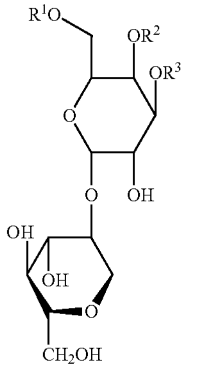

(In Formula 1, $R^1$, $R^2$ and $R^3$ are independently hydrogen atoms or $R^{Bz}$, and at least one of $R^1$, $R^2$ and $R^3$ is $R^{Bz}$, and the $R^{Bz}$ is Formula 2 below.)

[Formula 2]

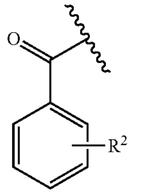

(In Formula 2, $R^2$ is hydrogen atom, halogen, a cyano group, a nitro group, an azide group, a phenyl group, a 5-6 membered heterocyclic group containing one or more heteroatoms selected from the group consisting of N, O and S, a $C_{1-6}$ alkyl group, a $C_{1-6}$ alkoxy group, a $C_{1-6}$ alkylthio group, a $C_{2-6}$ alkenyl group, a $C_{2-6}$ alkynyl group, or a pharmaceutically acceptable salt.).

Advantageous Effects

The present invention relates to a composition exhibiting an excellent prophylactic or therapeutic effect on cancer, the composition comprising polygalatenoside, an optical isomer thereof, or a pharmaceutically acceptable salt thereof as an active ingredient. The polygalatenoside of the present invention has the effects of suppressing reactive oxygen, inhibiting NOX2 protein activity, killing cancer cells, and repressing cancer cell growth to exhibit a prophylactic, alleviative, or therapeutic effect on cancer.

The present invention provides a food composition for improvement exhibiting an anti-aging or antioxidant effect including polygalatenoside, an optical isomer thereof, or a pharmaceutically acceptable salt thereof as an active ingredient. Further, the present invention provides a cosmetic composition for improvement exhibiting an anti-aging or antioxidant effect including polygalatenoside, an optical isomer thereof, or a pharmaceutically acceptable salt thereof as an active ingredient.

DESCRIPTION OF DRAWINGS

FIG. 1 is a diagram illustrating an effect of suppressing reactive oxygen according to polygalatenoside treatment of the present invention.

FIG. 2 is a diagram illustrating an effect of inhibiting NOX2 protein activity according to polygalatenoside treatment of the present invention.

FIG. 3 is a diagram illustrating an effect of killing cancer cells according to polygalatenoside treatment of the present invention.

FIG. 4 is a diagram illustrating an effect of repressing cancer cell growth according to polygalatenoside treatment of the present invention.

BEST MODE FOR THE INVENTION

The present invention provides a pharmaceutical composition for prevention or treatment of cancer including polygalatenoside as a compound represented by Formula 1 below, an optical isomer thereof, or a pharmaceutically acceptable salt thereof as an active ingredient.

[Formula 1]

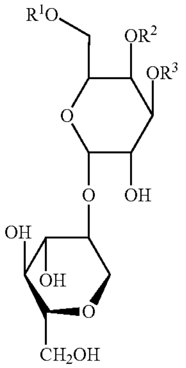

(In Formula 1, $R^1$, $R^2$ and $R^3$ are independently hydrogen atoms or $R^{Bz}$, and at least one of $R^1$, $R^2$ and $R^3$ is $R^{Bz}$, and the $R^{Bz}$ is Formula 2 below.)

[Formula 2]

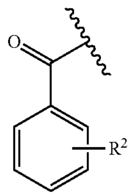

(in Formula 2, $R^2$ is H (hydrogen atom), halogen, a cyano group, a nitro group, an azide group, a phenyl group, a 5-6 membered heterocyclic group containing one or more heteroatoms selected from the group consisting of N, O and S, a $C_{1-6}$ alkyl group, a $C_{1-6}$ alkoxy group, a $C_{1-6}$ alkylthio group, a $C_{2-6}$ alkenyl group, a $C_{2-6}$ alkynyl group, or a pharmaceutically acceptable salt.)

In the present invention, when in Formula 1, $R^1$=$R^{Bz}$, and $R^2$=$R^3$=H, and in Formula 2, $R^2$=H, the compound is polygalatenoside A represented by Formula 3 below.

[Formula 3]

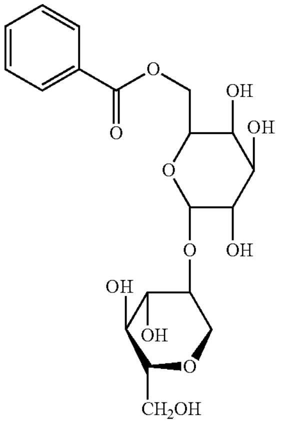

In the present invention, when in Formula 1, $R^1$=$R^2$=H, $R^3$=$R^{Bz}$, and in Formula 2, $R^2$=H, the compound is polygalatenoside B represented by Formula 4 below.

[Formula 4]

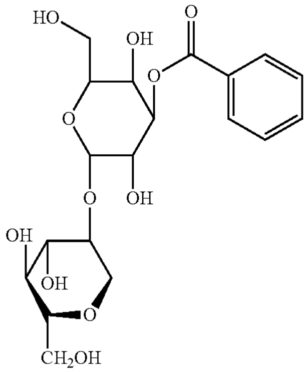

In the present invention, when in Formula 1, $R^1$=$R^3$=H, $R^2$=$R^{Bz}$, and in Formula 2, $R^2$=H, the compound is polygalatenoside C represented by Formula 5 below.

[Formula 5]

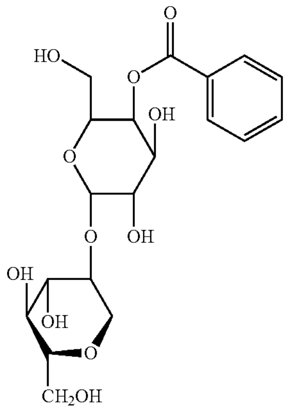

The polygalatenoside of the present invention has an antioxidant effect by suppressing reactive oxygen and may protect cells from aging caused by oxidative stress and prevent aging-related diseases. The aging-related disease may be any one selected from the group consisting of diabetes, myocardial infarction, angina pectoris, atherosclerosis, and heart failure. In addition, the polygalatenoside of the present invention may be applied to a food composition or a cosmetic composition for improvement exhibiting an anti-aging or antioxidant effect due to the suppressive effect on reactive oxygen.

The polygalatenoside of the present invention may induce the death of cancer cells, such as prostate cancer, pancreatic cancer, melanoma, glioma, breast cancer, bladder cancer, colon cancer, and ovarian cancer by inhibiting NOX2 protein activity.

In addition, it was confirmed that the polygalatenoside of the present invention had an anticancer effect by exhibiting effects of killing cancer cells and repressing cancer cell growth.

In the present invention, experiments were individually performed at least three times, and data from three experiments were expressed as mean±standard deviation (SD). Data analysis was performed using GraphPad PRISM software and Microsoft Excel software. Statistical significance (p value) was calculated using an ANOVA with Tukey's multiple comparisons test. When the p value was less than 0.05, it was considered statistically significant, and in the drawing, the p value was indicated as less than 0.05*, less than 0.01, less than 0.001*, and less than 0.0001****.

Throughout this specification, '%' used to indicate the concentration of a specific material is solid/solid (w/w) %, solid/liquid (w/v) %, and liquid/liquid (v/v) %, unless otherwise stated.

In the present invention, the pharmaceutical composition may further include an adjuvant in addition to the active ingredient. Any adjuvant known in the art may be used as the adjuvant without limitation.

The pharmaceutical composition according to the present invention may be prepared in the form of incorporating the active ingredients into a pharmaceutically acceptable carrier. Here, the pharmaceutically acceptable carrier includes carriers, excipients and diluents commonly used in a pharmaceutical field. The pharmaceutically acceptable carrier that may be used in the pharmaceutical composition of the present invention is not limited thereto, but may include lactose, dextrose, sucrose, sorbitol, mannitol, xylitol, erythritol, maltitol, starch, acacia gum, alginate, gelatin, calcium phosphate, calcium silicate, cellulose, methylcellulose, polyvinylpyrrolidone, water, methyl hydroxybenzoate, propyl hydroxybenzoate, talc, magnesium stearate, and mineral oil.

The pharmaceutical composition of the present invention may be formulated and used in the form of oral formulations, such as powders, granules, tablets, capsules, suspensions, emulsions, syrups, aerosols, etc., external preparations, suppositories, and sterile injectable solutions according to each conventional method.

The formulations may be prepared by using diluents or excipients, such as a filler, an extender, a binder, a wetting agent, a disintegrating agent, a surfactant, etc., which are generally used. Solid formulations for oral administration include tablets, pills, powders, granules, capsules, etc., and these solid formulations may be prepared by mixing at least one excipient, for example, starch, calcium carbonate, sucrose, lactose, gelatin, etc. with the active ingredients. Further, lubricants such as magnesium stearate and talc may be used in addition to simple excipients. Liquid formulations for oral administration may correspond to suspensions, oral liquids, emulsions, syrups, etc., and may include various excipients, for example, a wetting agent, a sweetener, an aromatic agent, a preserving agent, etc., in addition to the commonly used diluents, such as water and liquid paraffin. Formulations for parenteral administration include sterile aqueous solutions, non-aqueous solvents, suspensions, emulsions, lyophilized agents, and suppositories. As the non-aqueous solvent and the suspension, propylene glycol, polyethylene glycol, vegetable oil such as olive oil, injectable ester such as ethyl oleate, etc. may be used. As the base of the suppository, witepsol, Tween 61, cacao butter, laurinum, glycerogelatin, etc. may be used.

The pharmaceutical composition of the present invention may be administered to a subject through various routes. All methods of administration may be expected, and the pharmaceutical composition may be administered, for example, orally, intravenously, intramuscularly, subcutaneously, or by intraperitoneal injection.

The pharmaceutical composition of the present invention may be formulated into various oral or parenteral dosage forms.

Formulations for oral administration include, for example, tablets, pills, hard and soft capsules, solutions, suspensions, emulsifiers, syrups, granules, etc., and these formulations may further include diluents (e.g., lactose, dextrose, sucrose, mannitol, sorbitol, cellulose and/or glycine), lubricants (e.g., silica, talc, stearic acid and its magnesium or calcium salts and/or polyethylene glycol), in addition to the active ingredient. In addition, the tablets may contain a binder such as magnesium aluminum silicate, starch paste, gelatin, tragacanth, methylcellulose, sodium carboxymethylcellulose and/or polyvinylpyrrolidine, and in some cases, may contain disintegrants or effervescent mixtures such as starch, agar, alginic acid or its sodium salt and/or an absorbent, a coloring agent, a flavoring agent, and a sweetening agent. The formulations may be prepared by conventional mixing, granulating, or coating methods.

In addition, a typical formulation for parenteral administration is an injection formulation, and as a solvent for the injection formulation, water, a Ringer's solution, isotonic physiological saline, or a suspension may be used. Sterile fixed oils of the injection formulation may be used as a solvent or suspension medium, and any non-irritating fixed oil including mono- and di-glycerides may also be used for this purpose.

In addition, the injection formulation may use fatty acids such as oleic acid.

In addition, the food composition for improvement according to the present invention may contain various flavoring agents, natural carbohydrates, or the like as additional ingredients, like conventional food composition, in addition to containing polygalatenoside, an optical isomer thereof, or a pharmaceutically acceptable salt thereof as the active ingredient.

Examples of the above-described natural carbohydrates include general sugars, including monosaccharides, such as glucose, fructose, etc.; disaccharides, such as maltose, sucrose, etc.; and polysaccharides, such as dextrin, cyclodextrin, etc., and sugar alcohols such as xylitol, sorbitol, erythritol, etc. The above-described flavoring agents may be advantageously used with natural flavoring agents (tauumatin), *stevia* extracts (e.g., rebaudioside A, glycyrhizin, etc.), and synthetic flavoring agents (saccharin, aspartame, etc.). The food composition of the present invention may be formulated in the same manner as the following pharmaceutical composition to be used as a functional food or added to various foods. The food that may be added with the composition of the present invention may include, for example, beverages, meat, chocolate, foods, confectionery, pizza, ramen, other noodles, gums, candies, ice creams, alcoholic beverages, vitamin complexes, health food supplements, and the like.

In addition, the food composition may contain various nutrients, vitamins, minerals (electrolytes), flavoring agents such as synthetic and natural flavoring agents, coloring agents and enhancers (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonating agent used in a carbonated drink, and the like, in addition to polygalatenoside, an optical isomer thereof, or a pharmaceutically acceptable salt thereof as the active ingredient. In addition, the food composition of the present invention may contain natural fruit juice, and pulps for preparing fruit juice beverages and vegetable beverages.

The food composition for improvement according to the present invention may be prepared and processed in the form of tablets, capsules, powders, granules, liquids, pills, and the like. In the present invention, the 'health functional food composition' refers to foods prepared and processed by using raw materials or ingredients with functionality, which are useful for the human body according to Act No. 6727 on Health Functional Foods, and means foods taken for adjusting nutrients for the structures and functions of the human body or obtaining a useful effect on health applications such as physiological actions. The food composition of the present invention may include conventional food additives, and the suitability as the food additives is determined by the specifications and standards for the corresponding item in accordance with the general rules of the Food Additive Codex, general test methods, and the like approved by the Food and Drug Administration, unless otherwise specified. The items disclosed in the "Food Additives Codex" may include, for example, chemical composites such as ketones, glycine, calcium citrate, nicotinic acid, cinnamic acid, etc.; natural additives such as desensitizing dye, licorice extract, crystal cellulose, Kaoliang color, guar gum, etc.; mixed formulations such as sodium L-glutamic acid formulations, noodle additive alkali agents, preservative formulations, tar color formulations, etc. For example, the health functional food in the form of tablets may be formed by granulating a mixture mixed with the active ingredient of the present invention and an excipient, a binder, a disintegrant, and other additives by conventional methods, and then compression-molding the mixture by adding a slip modifier and the like, or directly compression-molding the mixture. In addition, the food composition in the form of tablets may contain a flavor enhancer or the like as needed. In the food composition in the form of capsules, hard capsules may be prepared by filling conventional hard capsules with a mixture mixed with the active ingredient of the present invention and additives such as excipients, etc. Soft capsules may be prepared by filling a capsule base such as gelatin with a mixture mixed with the active ingredient of the present invention and additives such as excipients, etc. The soft capsules may contain a plasticizer such as glycerin or sorbitol, a colorant, a preservative, and the like, if necessary. The health functional food in the form of pills may be prepared by molding a mixture mixed with the active ingredient of the present invention and an excipient, a binder, a disintegrant, etc. by conventional known methods, and may also be coated with white sugar or other coating agents or surface-coated with materials such as starch and talc, if necessary. The food composition in the form of granules may be prepared by granulating a mixture mixed with the active ingredient of the present invention and an excipient, a binder, a disintegrant, etc. by conventional known methods and may contain a flavoring agent, a flavor enhancer, etc., if necessary.

In addition, the cosmetic composition for improvement according to the present invention may be prepared by including polygalatenoside, an optical isomer thereof, or a pharmaceutically acceptable salt thereof in a cosmetically effective amount, and a cosmetically acceptable carrier.

As used herein, the cosmetically effective amount refers to an amount sufficient to achieve the anti-aging or antioxidant effect of the composition of the present invention described above.

The appearance of the cosmetic composition contains a cosmetically or dermatologically acceptable medium or base. The appearance of the cosmetic composition may be provided in all formulations suitable for local application, for example, solutions, gels, solids, pasty anhydrous products, emulsions obtained by dispersing an oil phase in a water phase, suspensions, microemulsions, microcapsules, microgranules or ionic (liposomes) and non-ionic vesicular dispersions, or creams, toners, lotions, powders, ointments, sprays, or concealer sticks. These compositions may be prepared according to conventional methods in the art. The composition according to the present invention may also be used in the form of a foam or in the form of an aerosol composition further containing a compressed propellant.

The cosmetic composition according to an embodiment of the present invention is not particularly limited in its formulation, and may be formulated in cosmetics, such as softening lotion, astringent lotion, nourishing lotion, nourishing cream, massage cream, essence, eye cream, eye essence, cleansing lotion, cleansing foam, cleansing water, pack, powder, body lotion, body cream, body oil, and body essence.

When the formulation of the cosmetic composition of the present invention is the paste, cream, or gel, as carrier ingredients, animal oils, vegetable oils, wax, paraffin, starch, tragacanth, cellulose derivatives, polyethylene glycol, silicone, bentonite, silica, talc, zinc oxide or the like may be used.

When the formulation of the cosmetic composition of the present invention is the powder or spray, as the carrier ingredients, lactose, talc, silica, aluminum hydroxide, calcium silicate or polyamide powder may be used, and particularly, in the case of the spray, a propellant such as chlorofluorohydrocarbon, propane/butane or dimethyl ether may be additionally included.

When the formulation of the cosmetic composition of the present invention is the solution or emulsion, as the carrier ingredients, a solvent, a solubilizing agent or an emulsifying agent may be used. For example, the carrier ingredients include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or fatty acid ester of sorbitan.

When the formulation of the cosmetic composition of the present invention is the suspension, as the carrier ingredients, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar, tragacanth, or the like may be used.

When the formulation of the cosmetic composition of the present invention is the surfactant-containing cleansing, as the carrier ingredients, aliphatic alcohol sulfate, aliphatic alcohol ether sulfate, sulfosuccinic acid monoester, isethionate, imidazolinium derivatives, methyltaurate, sarcosinate, fatty acid amide ether sulfate, alkylamido betaine, aliphatic alcohol, fatty acid glyceride, fatty acid diethanolamide, vegetable oil, lanolin derivatives, ethoxylated glycerol fatty acid ester, or the like may be used.

The cosmetic composition of the present invention may be applied with cosmetics, such as toner, lotion, cream, essence, pack, foundation, color cosmetics, sunscreen, two-way cake, face powder, compact, makeup base, skin cover, eye shadow, lipstick, lip gloss, lip fix, eyebrow pencil, and tonic, and cleaning agents, such as shampoo and soap.

The cosmetic composition according to an embodiment of the present invention may further include functional additives and ingredients included in general cosmetic compositions, in addition to polygalatenoside, the optical isomer thereof, or the pharmaceutically acceptable salt thereof. The functional additives may include ingredients selected from the group consisting of water-soluble vitamins, oil-soluble vitamins, polymer peptides, polymer polysaccharides, sphingolipids, and seaweed extract.

In addition to the functional additives, the cosmetic composition of the present invention may also be mixed with ingredients included in general cosmetic compositions, if necessary. Other mixed ingredients to be included may include oil and fat ingredients, moisturizers, emollients, surfactants, organic and inorganic pigments, organic powders, ultraviolet absorbers, preservatives, disinfectants, antioxidants, plant extracts, pH adjusters, alcohols, pigments, fragrances, blood circulation accelerators, cooling agents, diaphoretic, purified water, and the like.

MODES OF THE INVENTION

Hereinafter, the present invention will be described in more detail through Examples and Experimental Examples. However, the following Examples and Experimental Examples are presented as examples for the present invention, and when it is determined that a detailed description of well-known technologies or configurations known to those skilled in the art may unnecessarily obscure the gist of the present invention, the detailed description thereof may be omitted, and the present invention is not limited thereto. Various modifications and applications of the present invention are possible within the description of claims to be described below and the equivalent scope interpreted therefrom.

<Preparation Example 1> Culture of Melanoma Cells

B16-F10 melanoma cells were cultured under conditions of 36.5° C. and 5% $CO_2$ using a Dulbecco's modified Eagle's medium supplemented with 10% (v/v) fetal bovine serum and 1% (v/v) penicillin-streptomycin.

<Preparation Example 2> Preparation of Compound Represented by Formula 3 (Polygalatenoside A)

Polygalatenoside A (Cat. #SMB00542-1MG) from Sigma-Aldrich was dissolved in dimethyl sulfoxide at a final concentration of 2 mM and used in the following experiment.

<Experimental Example 1> Confirmation of Effect of Suppressing Reactive Oxygen by Polygalatenoside In general, ROS is known to be involved in the regulation of cell survival and differentiation within normal cells, and a high level of ROS reacts with genes or proteins of cells to cause damage or mutation, thereby causing cancer. Cancer cells are known to maintain the high ROS level and known to inhibit the expression or activity of antioxidant genes and proteins, such as superoxide dismutase (SOD), glutathione peroxidase (GPx), glutathione, and vitamin C, compared to normal cells. The ROS is mainly produced in the mitochondria in cells, and it is considered that the ROS inhibits the mitochondrial metabolism of cancer cells by reducing the ROS level of cancer cells, and thus interferes with the metabolic functions of cancer cells. In addition, the ROS is not only involved in the metabolism, development, and metastasis of cancer cells, but also plays an important role in development of inflammation that causes cancer.

It is known that oxidative stress in cells generated by ROS plays a role in the expression of several cancer-related genes, such as nuclear factor-kappa B (NF-kB), p53, β-catenin/Wnt, and activator protein 1 (AP-1). In addition, the expression of these genes is associated with inflammation-related cytokines or genes that regulate the cell cycle. In addition, NF-kB is activated to increase the production of interleukin (IL)-1 or IL-6, which plays an important role in the inflammatory response, which affects the metastasis and growth of cancer cells. In addition, an increase in ROS is also associated with actin cytoskeleton reorganization of cells to be associated with the migration and metastasis of cancer cells.

Melanoma occurs frequently in the skin, and when cells are exposed to ultraviolet rays, oxidative stress occurs to increase the generation of reactive oxygen and inhibit the generation of antioxidant enzymes such as SOD. It is known that when ROS generation is increased in B16-F10 cells, metastasis is increased, but when Rac1 is activated and WAVE2 is expressed by ROS, actin polymerization occurs to affect cell migration. It has been reported that when ROS is decreased, Rac1 activity and the expression of WASP-family verprolin-homologous protein 2 (WAVE2) are decreased to suppress the metastasis due to increased ROS (Sun joo Park et al., Antioxidant Dieckol Downregulates the Rac1/ROS Signaling Pathway and Inhibits Wiskott-Aldrich Syndrome Protein (WASP)-Family Verprolin-Homologous Protein 2 (WAVE2)-Mediated Invasive Migration of B16 Mouse Melanoma Cells. Mol. Cells, 33(4): 363-369, 2012 April.).

Therefore, in the experiment, the effect of polygalatenoside on ROS in cells was confirmed.

B16-F10 melanoma cells were cultured for 12 hours, and then treated with polygalatenoside A at concentrations of 0, 0.1, 0.3, 1, 3, and 10 μM for 24 hours, respectively. Thereafter, the cells were treated with 2',7'-dichlorodihydrofluorescein diacetate ($H_2$DCFDA) at a concentration of 1 μM for 30 minutes, and the cells were washed with phosphate-buffered saline (PBS; pH 7.4). The cells were collected, and median fluorescence intensity (DCF-MFI) was measured using flow cytometry, and the results were shown in FIG. 1. The flow cytometry was performed using a Guava EasyCyte flow cytometer, GuavaIncyte software, and FlowJo software.

As shown in FIG. 1, it was shown that the level of intracellular reactive oxygen decreased with treatment of polygalatenoside A, and as the treatment concentration of polygalatenoside A increased, the reactive oxygen inhibition effect tended to increase.

Therefore, it was confirmed that the polygalatenoside of the present invention had an antioxidant effect by suppressing reactive oxygen. In addition, the polygalatenoside had a prophylactic or therapeutic effect on cancer caused by oxidative stress, and effects of repressing cancer cell growth and metastasis, and may prevent or treat diseases caused by oxides generated by reactive oxygen.

<Experimental Example 2> Confirmation of Effect of Inhibiting NOX Protein Activity by Polygalatenoside In the experiment, an anticancer effect of polygalatenoside on melanoma was confirmed through an effect of inhibiting NOX protein activity by polygalatenoside.

NOX is a membrane-bound enzyme and a major cause of oxidative stress that uses oxygen as a catalyst to generate reactive oxygen and is associated with various diseases. The activity of NOX increases with aging and causes serious oxidative stress in the cardiovascular system. The NOX may regulate the growth and death in cancer cells, such as prostate cancer, pancreatic cancer, melanoma, glioma, breast cancer, bladder cancer, colon cancer, and ovarian cancer. Therefore, in the experiment, the effect of polygalatenoside on NOX protein activity was confirmed.

B16-F10 melanoma cells were cultured for 12 hours, and then treated with polygalatenoside A at concentrations of 0, 0.1, 0.3, 1, 3, and 10 μM for 24 hours, respectively. Thereafter, the cells were washed twice with PBS, and collected, and proteins were recovered by lysing the cells with a radioimmunoprecipitation assay (RIPA) buffer containing phenylmethylsulfonyl fluoride (PMSF). 50 μg of proteins was separated by sodium dodecyl sulfate poly-acrylamide gel electrophoresis (SDS-PAGE) and then transferred to a polyvinylidene fluoride (PVDF) membrane. The membrane was treated with a tris-buffered saline (TBS; pH 7.6) containing 5% (w/v) skim milk, 0.05% (v/v) tween-20, and 0.01% (w/v) sodium azide at 25° C. for 1 hour. The membrane was washed three times with TBST (TBS containing 0.05% (v/v) tween-20) and treated with an anti-NOX2 primary antibody and a horse radish peroxidase (HRP)-conjugated secondary antibody. The protein levels were visualized using enhanced chemiluminescence (ECL) and an X-ray film. The expression level of NOX2 protein compared to β-actin was shown in FIG. 2 through a densitometry of ImageJ software.

As shown in FIG. 2, it was shown that the expression of NOX2 was increased by treatment with polygalatenoside A compared to an untreated control group (0 μM), and when treated with 3 μM polygalatenoside A, the expression of NOX2 was increased about 1.4 times compared to the untreated control group. Since the increase in protein expression due to drug treatment was a result of showing a possibility of acting as an inhibitor for the corresponding protein, it was shown that the polygalatenoside of the present invention exhibited an effect of inhibiting NOX2 protein.

That is, it was determined that the polygalatenoside of the present invention exhibited the effect of inhibiting NOX2 protein activity to induce the death of cancer cells, such as prostate cancer, pancreatic cancer, melanoma, glioma, breast cancer, bladder cancer, colon cancer, and ovarian cancer. In addition, since the polygalatenoside exhibits the effect of suppressing reactive oxygen according to the effect of inhibiting NOX2 protein activity, the polygalatenoside has a prophylactic or therapeutic effect on cancer caused by oxidative stress, and effects of repressing cancer cell growth and metastasis, and may prevent or treat diseases caused by oxides generated by reactive oxygen.

<Experimental Example 3> Confirmation of Anticancer Effect of Polygalatenoside In the experiment, an effect of killing melanoma cells by polygalatenoside was confirmed according to the effect of inhibiting NOX2 protein activity by polygalatenoside in Experimental Example 2.

B16-F10 melanoma cells were cultured in a 96-well cell culture plate for 12 hours, and then treated with polygalatenoside A at concentrations of 0, 0.1, 0.3, 1, 3, and 10 μM for 48 hours, respectively. The medium was treated with a WST8 Cell Viability Assay Reagent to a concentration of 10% (v/v) and cultured for 2 hours. Thereafter, cell viability was confirmed by measuring absorbance at 450 nm using a microplate reader, and the results were shown in FIG. 3.

As shown in FIG. 3, it was confirmed that a cell death effect was exhibited when treated with 3 μM polygalatenoside A.

Next, in order to measure changes in cell number, B16-F10 cells were cultured for 12 hours, and then treated with polygalatenoside A at concentrations of 0, 0.1, 0.3, 1, 3, and 10 μM for 72 hours, respectively. The cells were collected every 24 hours, stained with trypan blue, and the number of viable cells was measured using a hemocytometer, and the results were shown in FIG. 4.

As shown in FIG. 4, it was shown that the growth of melanoma cells was inhibited by treatment with polygalatenoside A, and particularly, in the case of treatment with 3 μM polygalatenoside A, the growth inhibition effect was the most significantly shown.

Therefore, it was confirmed that the polygalatenoside of the present invention had an anticancer effect by exhibiting effects of killing cancer cells and repressing cancer cell growth on melanoma.

The invention claimed is:

1. A method for treating cancer, the method comprising administering a pharmaceutical composition comprising a compound of Formula 1 below, an optical isomer thereof, or a pharmaceutically acceptable salt thereof as an active ingredient to a subject in need thereof

[Formula 1]

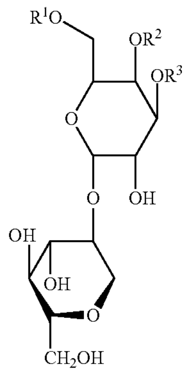

wherein in Formula 1,

R1, R2 and R3 are independently hydrogen atoms or RBz, and at least one of the R1, R2 and R3 is RBz, and the RBz is Formula 2 below,

[Formula 2]

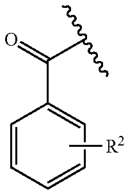

wherein in Formula 2,

R2 is hydrogen atom, halogen, a cyano group, a nitro group, an azide group, a phenyl group, a 5-6 membered heterocyclic group containing one or more heteroatoms selected from the group consisting of N, O and S, a C1-6 alkyl group, a C1-6 alkoxy group, a C1-6 alkylthio group, a C2-6 alkenyl group, a C2-6 alkynyl group, or a pharmaceutically acceptable salt.

2. The method of claim 1, wherein the compound is a compound of Formula 3 below

[Formula 3]

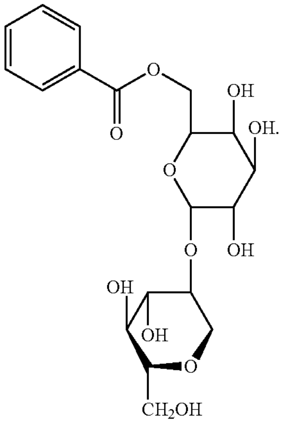

3. The method of claim 1, wherein the compound is a compound of Formula 4 below

[Formula 4]

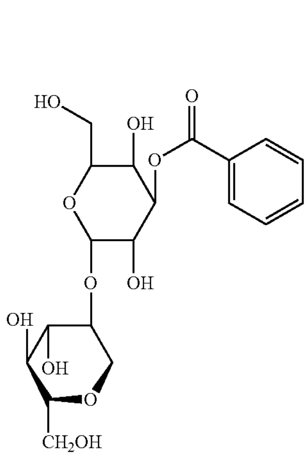

4. The method of claim 1, wherein the compound is a compound of Formula 5 below

[Formula 5]

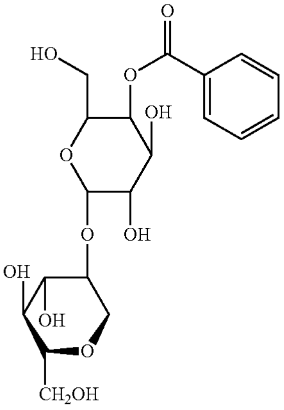

5. The method of claim 1, wherein the subject requires an antioxidant effect.

6. The method of claim 1, wherein the subject requires inhibiting NOX2 protein activity.

7. The method of claim 1, wherein the cancer is at least one selected from the group consisting of prostate cancer, pancreatic cancer, melanoma, glioma, breast cancer, bladder cancer, colon cancer, and ovarian cancer.

8. A method for alleviating cancer, the method comprising administering a food composition comprising a compound of Formula 1 below, an optical isomer thereof, or a pharmaceutically acceptable salt thereof as an active ingredient to a subject in need thereof

[Formula 1]

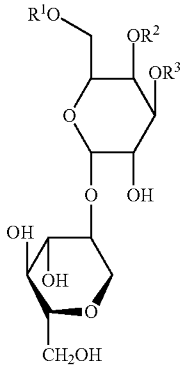

wherein in Formula 1,

R1, R2 and R3 are independently hydrogen atoms or RBz, and at least one of the R1, R2 and R3 is RBz, and the RBz is Formula 2 below

[Formula 2]

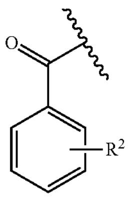

wherein in Formula 2,

R2 is hydrogen atom, halogen, a cyano group, a nitro group, an azide group, a phenyl group, a 5-6 membered heterocyclic group containing one or more heteroatoms selected from the group consisting of N, O and S, a C1-6 alkyl group, a C1-6 alkoxy group, a C1-6 alkylthio group, a C2-6 alkenyl group, a C2-6 alkynyl group, or a pharmaceutically acceptable salt.

9. The method of claim 8, wherein the subject requires an anti-aging or antioxidant effect

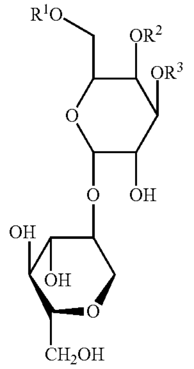

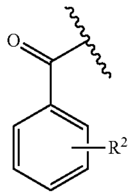

10. A method for improving exhibiting an anti-aging or antioxidant effect, the method comprising administering a cosmetic composition comprising a compound represented by Formula 1 below, an optical isomer thereof, or a pharmaceutically acceptable salt thereof as an active ingredient to a subject in need thereof

[Formula 1]

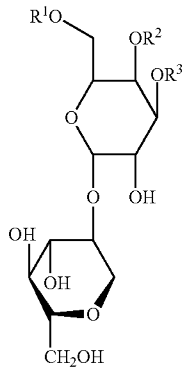

wherein in Formula 1,

R1, R2 and R3 are independently hydrogen atoms or RBz, and at least one of the R1, R2 and R3 is RBz, and the RBz is Formula 2 below

[Formula 2]

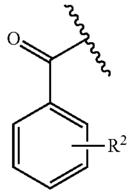

wherein in Formula 2,

R2 is hydrogen atom, halogen, a cyano group, a nitro group, an azide group, a phenyl group, a 5-6 membered heterocyclic group containing one or more heteroatoms selected from the group consisting of N, O and S, a C1-6 alkyl group, a C1-6 alkoxy group, a C1-6 alkylthio group, a C2-6 alkenyl group, a C2-6 alkynyl group, or a pharmaceutically acceptable salt.

* * * * *